US010765556B1

(12) United States Patent
Tarabishy

(10) Patent No.: US 10,765,556 B1
(45) Date of Patent: Sep. 8, 2020

(54) DEVICE AND METHOD FOR CLEARING INTRAOCULAR LENS CONDENSATION DURING VITRECTOMY

(71) Applicant: Ahmad Bakir Tarabishy, Seffner, FL (US)

(72) Inventor: Ahmad Bakir Tarabishy, Seffner, FL (US)

(*) Notice: Subject to any disclaimer, the term of this patent is extended or adjusted under 35 U.S.C. 154(b) by 199 days.

(21) Appl. No.: 15/897,197

(22) Filed: Feb. 15, 2018

(51) Int. Cl.
*A61F 9/00* (2006.01)
*A61F 9/007* (2006.01)
*A61F 9/009* (2006.01)
*A61F 9/008* (2006.01)

(52) U.S. Cl.
CPC .......... *A61F 9/00736* (2013.01); *A61F 9/009* (2013.01); *A61F 2009/00874* (2013.01)

(58) Field of Classification Search
CPC .................. A61F 9/00736; A61F 9/009; A61F 2009/00874
See application file for complete search history.

(56) References Cited

U.S. PATENT DOCUMENTS 701,278 A * 6/1902 Adcock
1,359,870 A * 11/1920 Buckland ............... A61B 17/50 606/161
4,075,730 A * 2/1978 Siemund ................... A47L 1/06 15/245
4,513,468 A * 4/1985 Hayden ................. B60S 1/3801 15/250.48
4,607,411 A * 8/1986 Lewis, Jr. .............. A46B 17/08 15/117
4,672,964 A * 6/1987 Dee .................... A61B 17/3213 30/321
4,924,882 A * 5/1990 Donovan ............... A61B 17/32 128/898
5,282,816 A * 2/1994 Miller ................ A61B 17/1659 606/167
5,451,230 A * 9/1995 Steinert ............... A61F 9/00736 606/1
5,817,119 A * 10/1998 Klieman ................ A61B 17/29 606/174
5,919,158 A 7/1999 Saperstein et al.
10,166,144 B2 * 1/2019 Depenbusch ....... A61F 9/00763
10,653,558 B2 * 5/2020 Kahook .............. A61F 9/00781
10,682,254 B2 * 6/2020 Kahook ............. A61B 17/3211
(Continued)

FOREIGN PATENT DOCUMENTS

EP 2005923 A1 * 12/2008 ......... A61F 9/00736

OTHER PUBLICATIONS

Jaffe, Glenn J. Management of Condensation on a Foldable Acrylic Intraocular Lens after Vitrectomy and Fluid-Air Exchange. American Journal of Ophthalmology, Nov. 1997, pp. 692-693.
(Continued)

*Primary Examiner* — Julian W Woo
(74) *Attorney, Agent, or Firm* — Michele L. Lawson; Smith & Hopen, P.A.

(57) ABSTRACT

A device and method for removing intraocular lens condensation is presented. The device is generally comprised of a handle attached to a shaft which is attached to a rubber-like blade. In use, the device is inserted into the eye so that the edge of the blade is in contact with the posterior surface of the lens. Movement of the blade in a downward motion removes condensation from the surgical viewing field.

17 Claims, 5 Drawing Sheets

(56) References Cited

U.S. PATENT DOCUMENTS

| | | | | |
|---|---|---|---|---|
| 2005/0149059 | A1* | 7/2005 | Tang | A61F 9/0133 606/107 |
| 2007/0282348 | A1* | 12/2007 | Lumpkin | A61F 9/00736 606/107 |
| 2018/0193191 | A1* | 7/2018 | Dam-Huisman | A61F 9/007 |

OTHER PUBLICATIONS

Browning, David J. Clinical Management of Silicone Introcular Condensation. American Journal of Ophthalmology, Apr. 2005, pp. 740-742.

* cited by examiner

DEVICE AND METHOD FOR CLEARING INTRAOCULAR LENS CONDENSATION DURING VITRECTOMY

FIELD OF THE INVENTION

This invention relates to a novel device and method for clearing intraoperative lens condensation. More particularly, it relates to a device and method that efficiently removes intraocular lens condensation during vitrectomy.

BACKGROUND OF THE INVENTION

Retinal detachment (RD) is a serious ocular condition in which the retina is separated from its underlying tissues. Retinal detachment is a common cause of severe vision loss. In retinal detachment, the retina pulls away from the underlying tissue layers which provide oxygen and metabolic support. Retinal detachment can occur when vitreous fluid leaks through a retinal hole or tear and collects underneath the retina. Tears or holes in the retina can occur for a number of reasons including disorders or aging that causes the retina to thin. A tear typically develops when there is a sudden collapse of the vitreous thus causing tugging on the retina with enough force to cause a tear. Fluid inside the vitreous may then travel through the tear and collect under the retina thus peeling it away from the underlying tissues which provide oxygen. In areas in which the retina is detached and the cells lack oxygen, vision may be lost if not treated quickly.

Rhegmatogenous retinal detachment is the most common etiology and is caused by a tear or hole that is usually in the peripheral retina.

Retinal detachment itself is painless, however symptoms are usually present before it occurs or advances. Symptoms of retinal detachment include the appearance of a large number of floaters; sudden flashes of light in the affected eye; and a shadow over a portion of the visual field that develops as the detachment progresses. Several conditions may increase the chance of retinal detachment including nearsightedness; previous cataract surgery; eye trauma; previous retinal detachment in the other eye; family history of retinal detachment; or weak areas in the retina. If left untreated, there is a very high chance of permanent vision loss.

Surgical repair, often emergent, is necessary to treat retinal detachment. Pars plana vitrectomy is the most commonly used method to repair RD. Vitrectomy involves removal of vitreous and all other tractional forces exerted on the torn retina and drainage of subretinal fluid, after which the eye is filled with a solution, such as a sterile saline solution. A fluid-gas exchange procedure is then performed in which the saline solution is removed at the same volumetric rate as a gas is injected. As the gas replaces the fluid, any subretinal fluid is squeezed from under the retina and can be removed with an extrusion cannula. Once all the saline solution is removed, the retinal tear or hole is treated using laser photocoagulation or cryoretinopexy. Finally, the fluid in the vitreous cavity is drained and replaced with either an expansive gas mixture or silicone oil.

Vitrectomy surgery is performed using an operating microscope, an endoilluminator probe, and a specialized wide-field lens system to allow for visualization of the retinal tissues. Sharp visualization is very important for the surgical success as precise intraoperative manipulation of tissues is required. Condensation of water or silicon droplets can develop on the posterior surface of an intraocular lens during the fluid-gas exchange can severely compromise the surgeon's view and make it difficult to impossible to see and repair the retinal detachment. Also, patients that have had a detached retina repaired using silicone oil can later develop adherent silicone oil bubbles to the posterior surface of their intraocular lens which can cause very blurred vision.

There are several strategies to deal with intraoperative lens condensation, none of which are very effective. Similarly, there are no simple methods to treat silicone oil bubbles adherent to an intraocular lens implant.

One strategy to deal with intraoperative lens condensation is the use of an aspiration cannula to remove the condensation. (Jaffe, 1997). In this method, the posterior surface of the intraocular lens is wiped with a soft-tipped aspiration cannula, or suction tube, which then aspirates the condensation through the cannula and out of the surgical field. This method only partially cleared the condensation in 6 of the 11 patients in which condensation occurred, however the condensation quickly reappeared to completely obscure the surgeon's vision after only a few minutes. Also, the tube is not specifically designed for this task. The suction tube is flaccid and does not allow for precise control or firm displacement.

Another method suggested injecting a balanced salt solution onto the posterior surface of the lens. However, this approach requires injecting fluid into a space in which the surgeon is trying to remove fluid. (Sappenfield, 1989)

Saperstein (U.S. Pat. No. 5,919,158) discloses an infusion cannula for use in clearing and preventing condensation on the posterior surface of an artificial lens during the fluid-gas exchange portion of a pars plana vitrectomy. In use, the infusion cannula redirects the flow of gas entering the eye toward the posterior surface of the lens with the moisture content and temperature of the gas supplied to the infusion cannula being controlled.

Using an intraocular irrigating solution or filling the anterior chamber of the eye with a warm viscoelastic fluid to warm the lens has been suggested to prevent condensation. However, these solutions require the constant manipulation of instruments to deliver the solution/fluid during surgery and can leave a film of the fluid on the posterior lens which distorts the surgeon's view.

Recently, a heating pad has been placed over the eye with lids closed for approximately 20 minutes to reduce condensation to allow the application of laser retinopexy. However, while the condensation was reduced in order to finish the surgery, the condensation reoccurred on the intraocular lens once the eye cooled thus not making this an effective solution. (Browning, 2005)

Given the disadvantages in the current techniques for dealing with intraoperative lens condensation, what is needed is a device and method which would allow for removal of intraoperative lens condensation.

SUMMARY OF INVENTION

The proposed device is designed specifically to address the removal of intraocular lens condensation. The main components include the blade, shaft, and handle. The blade is composed of a rubber-like material the edge of which is positioned to come in contact with the lens surface and is designed to displace condensation or silicone oil. The shaft connects the blade and the handle and extends into the eye. The handle allows for controlled manual manipulation.

A device for removing intraocular lens condensation is presented comprising: a handle having proximal and distal ends; a shaft having a proximal and a distal end wherein the proximal end of the shaft is attached to the distal end of the handle; and a rubber-like blade having a proximal and a distal end wherein the proximal end of the blade is attached to the distal end of the shaft wherein the blade has at least one longitudinal condensation removal edge.

In an embodiment, the blade is moveably attached to the shaft by a hinge and a blade deployment mechanism connected to the blade by a wire. The blade deployment mechanism can be a lever, a switch, a button, a wheel, or a slider to manually move the blade. In other embodiments, the blade deployment mechanism is connected to the blade electronically in which activation of the blade deployment mechanism, such as a switch, lever or button, deploys the blade. In embodiments in which a blade deployment mechanism is used, the shaft is straight.

In an alternative embodiment, the shaft is curved at the distal end by about 90°. This embodiment does not require the use of a blade deployment mechanism.

A method of removing intraocular lens condensation is also presented comprising: providing a device for removing intraocular lens condensation as described previously; inserting the device into the eye of a patient; positioning the device so that the condensation removal edge is in contact with a posterior surface of the lens; and moving the device in a downward motion across the posterior surface of the lens; wherein movement of the device across the posterior surface of the lens results in removal of the intraocular lens condensation from a surgical viewing field.

In embodiments in which a blade deployment mechanism is used, once the device is inserted into the eye of the patient, the blade deployment mechanism is engaged to move the blade to about a 90° angle prior to placement of the blade edge on the surface of the posterior lens and movement of the blade in a downward motion to remove the condensation.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
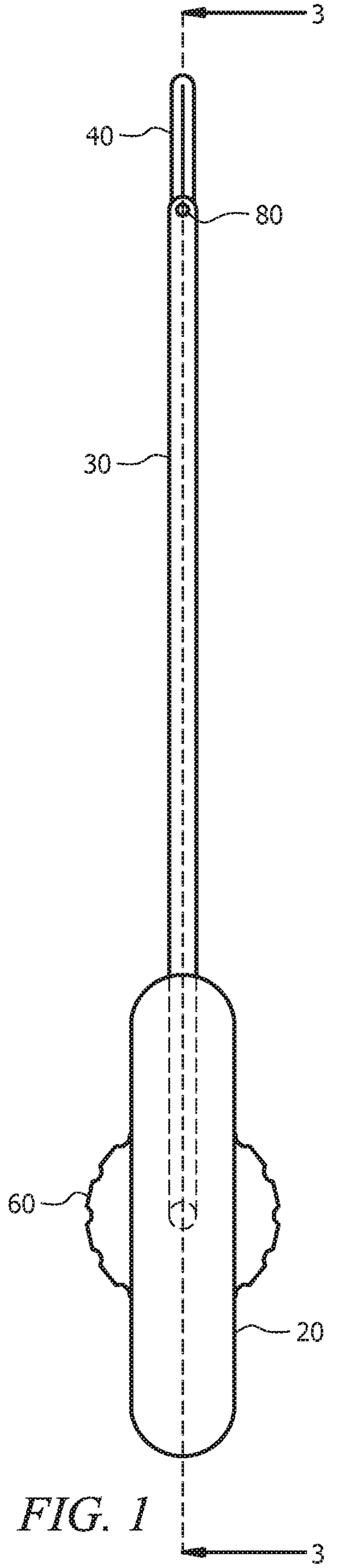
FIG. 1 is a front view of the device depicting the blade in an undeployed position and a wheel as the blade deployment mechanism.

In the following detailed description of the preferred embodiments, reference is made to the accompanying drawings, which form a part hereof, and within which are shown by way of illustration specific embodiments by which the invention may be practiced. It is to be understood that there are other embodiments by which the invention may be practiced. It is to be understood that other embodiments may be utilized and structural changes may be made without departing from the scope of the invention.

Definitions

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed in the invention. The upper and lower limits of these smaller ranges may independently be excluded or included within the range. Each range where either, neither, or both limits are included in the smaller ranges are also encompassed by the invention, subject to any specifically excluded limit in the stated range. Where the stated range includes one or both of the limits, ranges excluding either or both of those excluded limits are also included in the invention.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose. Where particular values are described in the application and claims, unless otherwise stated, the term "about" meaning within an acceptable error range for the particular value should be assumed. In some cases, the term "about" refers to +10%.

As used in the specification and claims, the singular form "a", "an" and "the" include plural references unless the context clearly dictates otherwise.

"Intraocular lens condensation" as used herein refers to liquid that forms on the posterior lens surface of the eye during or after vitrectomy. "Intraocular lens condensation" as used herein refers both to water condensation that forms as a result of fluid-gas exchange during or after surgery as well as silicon oil droplets that may form on the lens post-surgery which affects the patient's vision.

"Blade" as used herein refers to the part of the device which can be used for clearing or wiping liquid matter from a lens surface. The blade is a flexible elongated section of the device having at least one tapered edge for contacting the posterior surface of the lens. In some embodiments, the blade has a teardrop-shaped cross section in which the two opposing sides of a generally half-circular rounded side taper inwards towards each other to form a point/line where the opposing sides meet thus forming an edge. In some embodiments, edge may be bifurcated or trifurcated with one edge being longer than the other edges. Blade may take any shape as long as it is capable of forming at least one edge for efficiently wiping away condensation on the posterior lens surface without damaging the lens and capable of being inserted into the eye without damaging the eye.

Blade may be manufactured of a smooth, flexible, biocompatible material such as a heat resistant, strong, water resistant, elastic polymer including, but not limited to, silicone, natural and synthetic rubber, neoprene, latex, plastics, synthetic polyisoprene, polyurethane, nitrile, and thermoplastic elastomers and polymers.

Blade can be statically attached to distal end of shaft or in some embodiments in which movement of blade occurs, blade can be attached to distal end of shaft by a hinge which allows for movement of blade relative to the longitudinal axis of shaft.

"Edge" as used herein refers to the line or point at which two surfaces of the blade meet. Edge refers to a longitudinal condensation removal edge which, in use, is in contact with the posterior surface of the lens and can be moved on the surface of the lens to remove condensation or oil droplets from the viewing field of the surgeon.

"Rubber-like" as used herein refers to a biocompatible material having properties similar to rubber such as being smooth, flexible, strong, water resistant, heat resistant and elastic.

"Shaft" as used herein refers to an elongated tubular member positioned between and attached to the handle at one (proximal) end and the blade at the other (distal) end. Shaft can be manufactured of a rigid biocompatible metal such as stainless steel. In some embodiments, shaft is straight while in other embodiments shaft is curved at the distal end. If curved, shaft is preferably curved at about a 90° angle. Shaft can be curved between about 40° to about 150°.

In some embodiments, shaft may be hollow which allows components necessary for blade deployment mechanism to move blade to be stored within shaft. In embodiments which do not employ blade deployment mechanism, shaft may be solid.

In some embodiments, shaft may contain a channel in its side which can house blade when blade is positioned at 180°, i.e. adjacent the longitudinal axis of shaft.

"Handle" as used herein refers to the grip portion of the device, attached to the proximal end of the shaft, which the user holds. Blade deployment mechanism may be positioned within handle. In some embodiments, the handle and the shaft may be comprised of one piece of continuous material. In some embodiments, handle may be made of a rubber-like material while in other embodiments, handle may be made of a metal such as stainless steel. In some embodiments, handle may have an ergonomic grip.

"Blade deployment mechanism" as used herein refers to any mechanism which may be used to move blade in at least a 90° with respect to the longitudinal axis of the shaft. In some embodiments, the blade can move 180° where at 180°, length of blade is positioned adjacent to longitudinal axis of shaft (i.e. folded back against shaft) and at 0°, length of blade extends in a straight line from distal end of shaft along the longitudinal axis. In some embodiments, blade can move 360°.

Blade deployment mechanism includes, but is not limited to, a sliding mechanism, a lever, a button, a switch, a wheel or any other mechanism capable of moving the blade relative to the longitudinal axis of the shaft.

In some embodiments, blade deployment mechanism may not only control movement of blade at an angle, but also control retraction of blade into hollow cavity of shaft. In this embodiment, hinge would attach to a connection means such as an elongated rod housed within hollow cavity of shaft. Elongated rod would attach at proximal end to blade deployment mechanism and at opposite distal end to blade via hinge. Movement of blade deployment mechanism to a certain stop point would advance rod, and thus blade, out of hollow cavity. Further movement of blade deployment mechanism in the same direction, past stop point, would move blade around hinge to orient blade at an angle. In this embodiment, the rod would take the place of wire 70.

Movement of blade deployment mechanism may be manual or electric. If movement of the blade is done manually, the blade deployment mechanism would connect to a wire or other attachment which would connect the blade to the blade deployment mechanism whereby movement of the blade deployment mechanism would cause corresponding movement of the blade via movement of wire and hinge. Alternatively, if movement is done electronically, electric circuitry would be contained within handle and shaft of device with deployment of the blade deployment mechanism causing an electric current to be transmitted to the blade thus signaling movement of blade around hinge.

Figure 2:
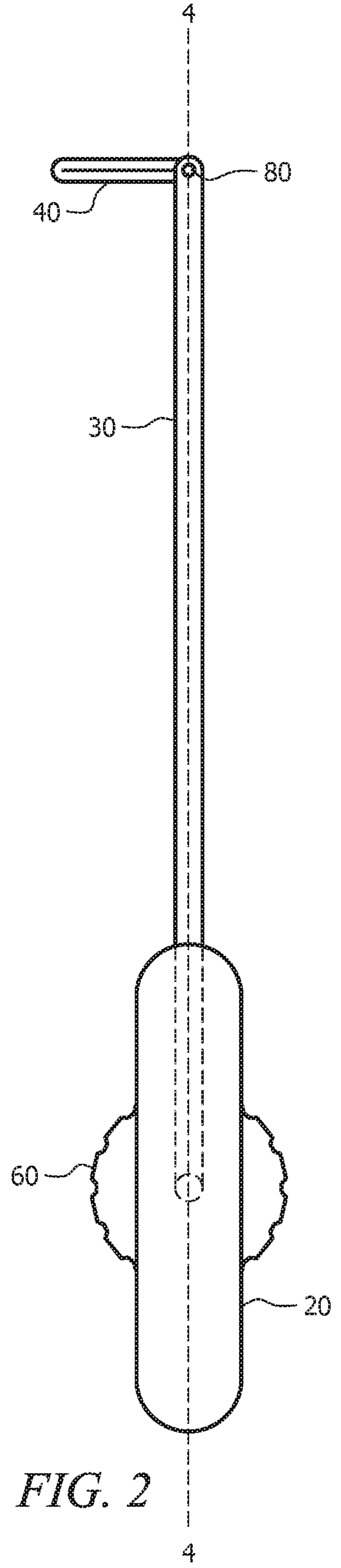
FIG. 2 is a front view of the device depicting the blade in a deployed position at an angle of about 90°.

"Longitudinal" or "longitudinal axis" as used herein, in terms of the device itself, refers to the line taken from distal end of blade to proximal end of handle. For example, distal end of blade to proximal end of blade would be the longitudinal axis of blade. Distal end of shaft to proximal end of shaft would be the longitudinal axis of shaft. Distal end of handle to proximal end of handle would be the longitudinal axis of handle. Longitudinal axis is shown in FIG. 2 as represented by line 4.

"Downward" as used herein refers to movement over the posterior surface of the lens in a direction from the upper lid of the eye towards the lower lid of the eye. Downward motion includes both motion in a straight or substantially straight line as well as angled motion for example, from the top left corner to the bottom right corner.

The present invention provides a device and method of treating intraocular lens condensation during vitrectomy. The device is generally comprised of a handle, a shaft, and a tapered flexible blade.

FIG. 1 illustrates one embodiment of device 10 in which blade 40 is shown as being attached via hinge 80 to shaft 30 which is in turn attached at its proximal end to handle 20. In this embodiment, shaft 30 is in a straight configuration with blade deployment mechanism 60 being shown positioned in handle 20. Blade 40 is shown in the undeployed position being in line with the longitudinal axis of shaft 30.

FIG. 2 illustrates the same embodiment shown in FIG. 1 except blade 40 is deployed in about a 90° angle. The embodiments illustrated in FIGS. 1 and 2 illustrate an embodiment with a wheel as blade deployment mechanism 60, however, as discussed above, other blade deployment mechanisms are contemplated by the invention as long as they are capable of moving blade 40 at an angle relative to longitudinal axis of shaft 30. Handle 20 and shaft 30 of this embodiment can be hollow to allow for blade deployment mechanism 60 to be positioned in handle 20 and for wire 70 to be contained within the hollow cavity of shaft 30.

Figure 3:
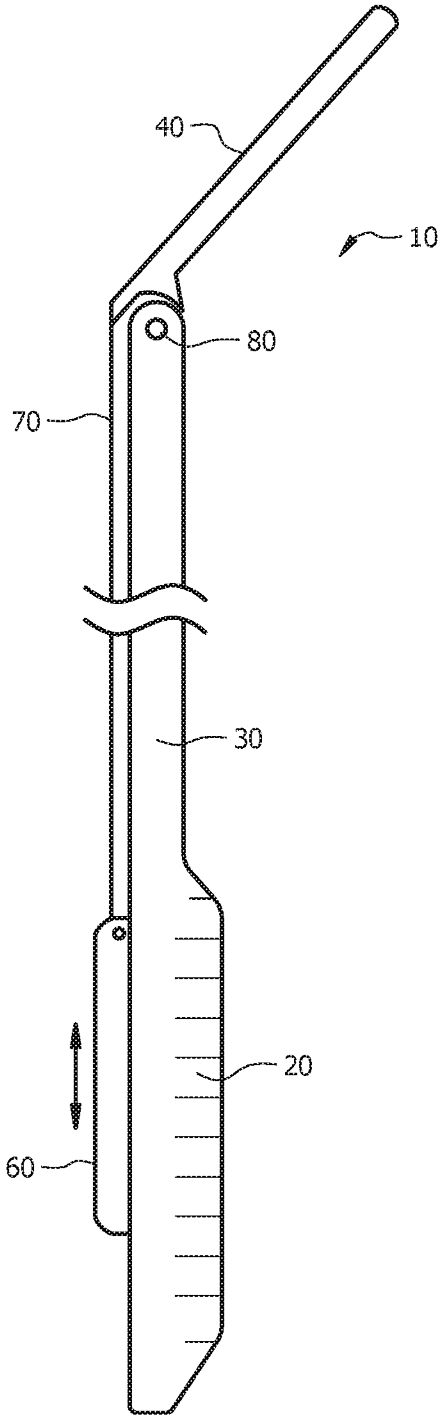
FIG. 3 is a cutaway view of the device along the longitudinal axis depicting one embodiment of the device in which a lever is used as the blade deployment mechanism to move the blade.

FIG. 3 is a longitudinal cutaway view of an embodiment of device 10 using a sliding lever as blade deployment mechanism 60. As shown in the figure, blade deployment mechanism 60 is connected to wire 70 at one end while the other end of wire 70 is connected to blade 40. Forward or backward movement of blade deployment mechanism 60 moves wire 70 which in turn correspondingly moves blade 40 around hinge 80 to orient blade 40 at an angle relative to the longitudinal axis of shaft 30. In some cases, this angle can be from between about 0° to about 90°.

Figure 4:
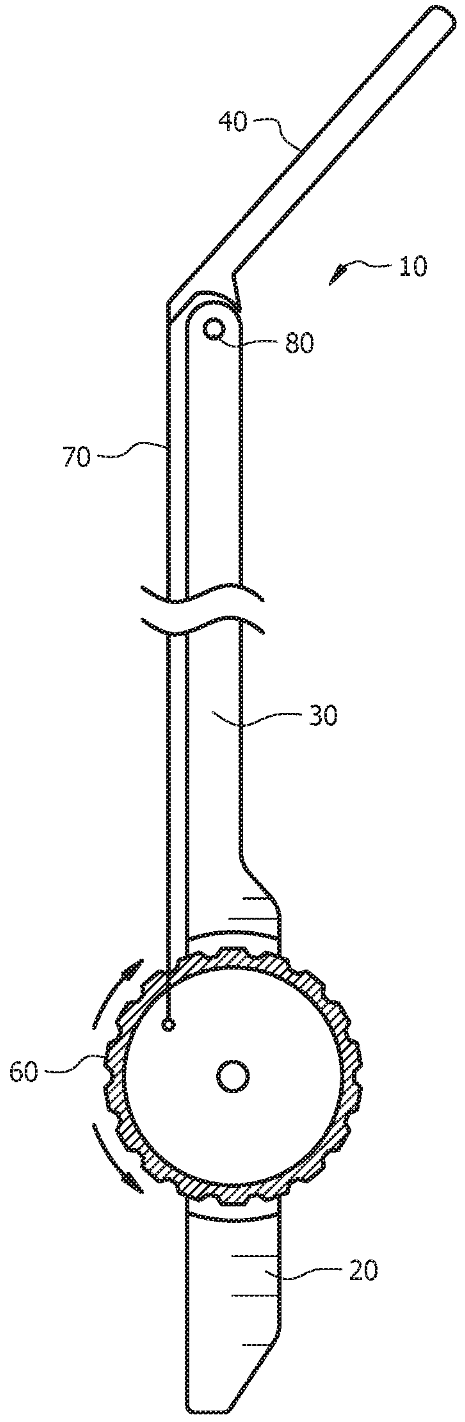
FIG. 4 is a cutaway view of the device along longitudinal axis 3 of FIG. 1 depicting one embodiment of the device in which a wheel is used as the blade deployment mechanism to move the blade.

FIG. 4 is an embodiment of device 10 illustrating a longitudinal cutaway view of FIG. 1 taken along line 3 of FIG. 1, using a wheel as blade deployment mechanism 60. As shown in the figure, blade deployment mechanism 60 is connected to wire 70 at one end while the other end of wire 70 is connected to blade 40. Clockwise or counter clockwise movement of blade deployment mechanism 60 moves wire 70 which in turn correspondingly moves blade 40 around hinge 80 to orient blade 40 at an angle relative to the longitudinal axis of shaft 30. In some cases, this angle can be from between about 0° to about 90°.

Figure 5:
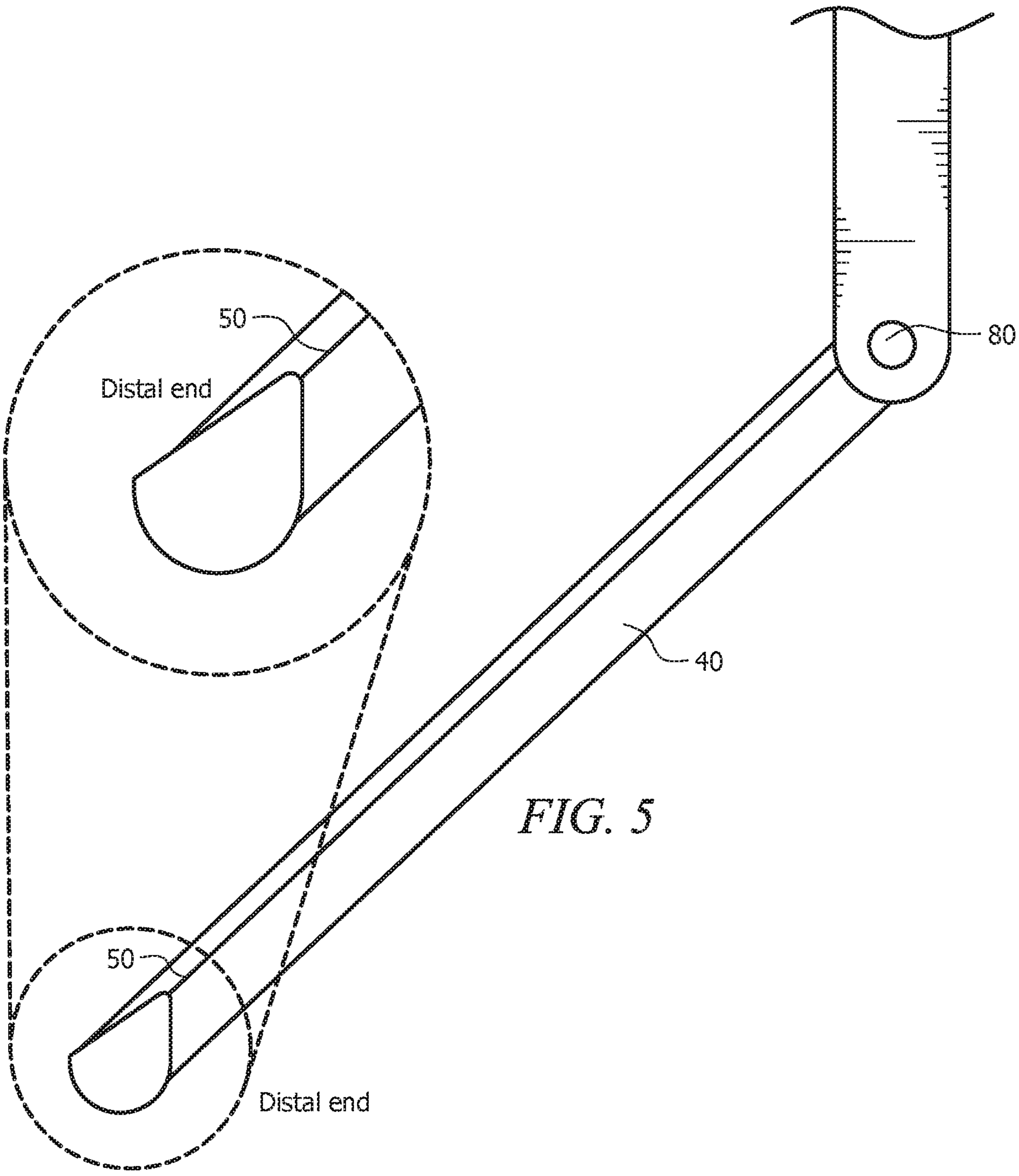
FIG. 5 is a magnified perspective view of the blade depicting the shape of the blade as well as the blade edge. The blade edge is pointed enough to remove the condensation on the lens but is not overly pointed (as a knife blade would be) so as to cause damage to the lens surface.

FIG. 5 is a magnified view of blade 40. Attachment of blade 40 to shaft 30 by hinge 80 is shown. In this embodiment, blade 40 has a cross-section having a general teardrop shape having a half-circular rounded side, the sides of which extend from the rounded side to taper inward to meet at a line/point to form edge 50. As discussed previously, blade 40 is preferably manufactured of a flexible biocompatible rubber-like material which can be used against the surface of the lens without damaging the lens.

Figure 6A:
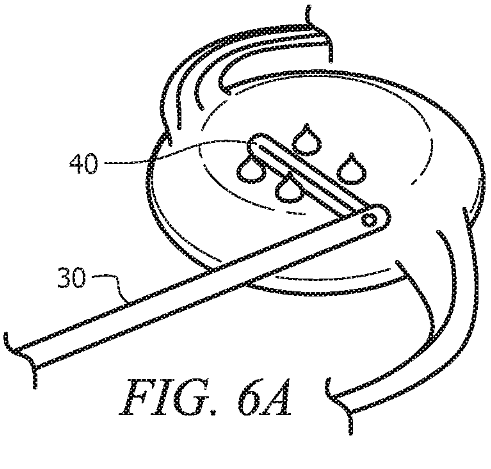
FIG. 6A-B are a series of images depicting removal of condensation droplets from the posterior surface of the lens using the straight shaft embodiment of the device described herein. (A) edge of blade is positioned perpendicularly against the lens surface; (B) movement of the blade in a downward motion clears the droplets from the lens surface thus clearing the viewing field.
Figure 6B:
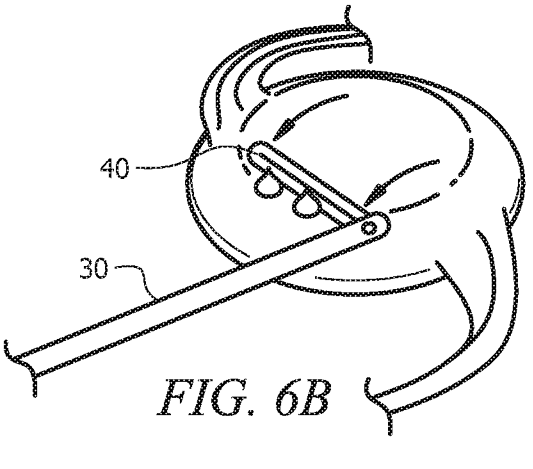
Figure 7:
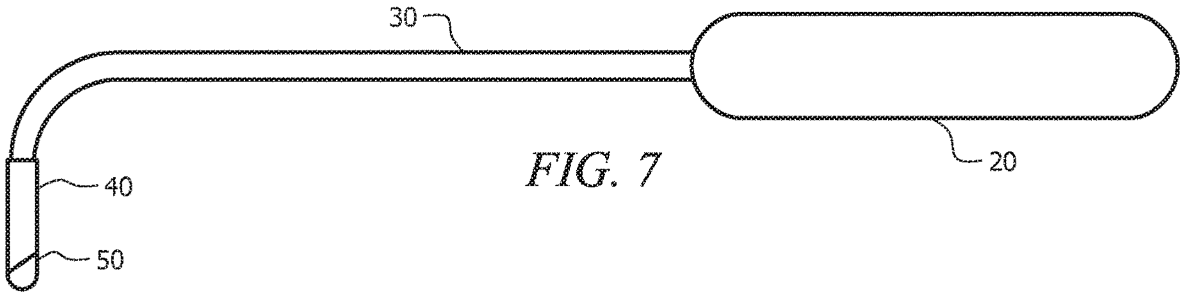
FIG. 7 is a front view of another embodiment of the device illustrating a curved shaft and static blade. No blade deployment mechanism is needed in this embodiment of the device.
Figure 8:
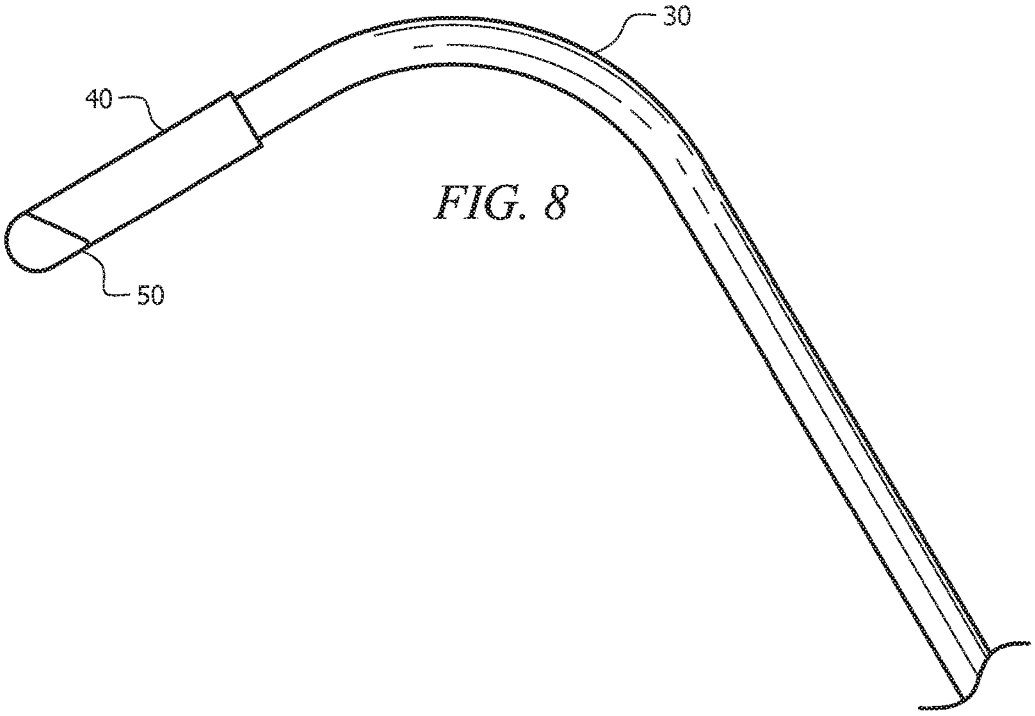
FIG. 8 is a magnified image of the curved shaft and static blade.

A method of removing intraocular lens condensation using device 10 is also presented. In use with the embodiment having blade deployment mechanism 60, the eye of the patient is first numbed then an eyelid speculum is used to keep the operative eye open while the other eye is covered. A surgical microscope with a lens allowing visualization of the inside of the eye as well as a magnified and detailed view. A vitrectomy probe is used to cut and remove the vitreous. Separate openings can be used to place instruments that assist in surgery. With regard to the device described herein, device 10 is inserted into the eye of the patient undergoing vitrectomy through a one of the openings with blade 40 undeployed, i.e. aligned with the longitudinal axis of device 10. Once inserted into the eye blade deployment mechanism 60 is moved to deploy blade 40 so that edge 50 is in contact with the posterior surface of the lens. Blade 40 is deployed to be oriented at an angle with respect to longitudinal axis of shaft 30. In some cases, this angle is about 90°. Once positioned, device 10 can be moved so that blade 40 moves in a downward motion, effectively wiping away any droplets from lens condensation out of the viewing field and towards drainage needles to remove the fluid from the eye. While movement of blade 40 is described as being in a downward motion, other motions are contemplated including upwards, across from one side to the other, and at an angle from top to bottom or vice versa, depending on where the drainage needles are positioned. In most cases, downward motion, whether angled or straight, is preferred as the fluid can be collected in the lower lid and easily removed. FIG. 6A-B are images depicting movement of device 10 once inserted into the eye of the patient. FIG. 6A depicts positioning of edge 50 of blade 40 against the posterior surface of the lens among the droplets. FIG. 6B depicts movement of blade 40 in a downward motion to remove droplets from the viewing field.

Alternatively, blade deployment mechanism 60 can be engaged to move blade 40 at varying angles from about 90° to about 180° to essentially wipe away the droplets/condensation to collect in the lower lid for drainage. In this embodiment, the length of blade 40 must be such that it stops short and does not contact lower lid when in the 180° position.

Figure 9:
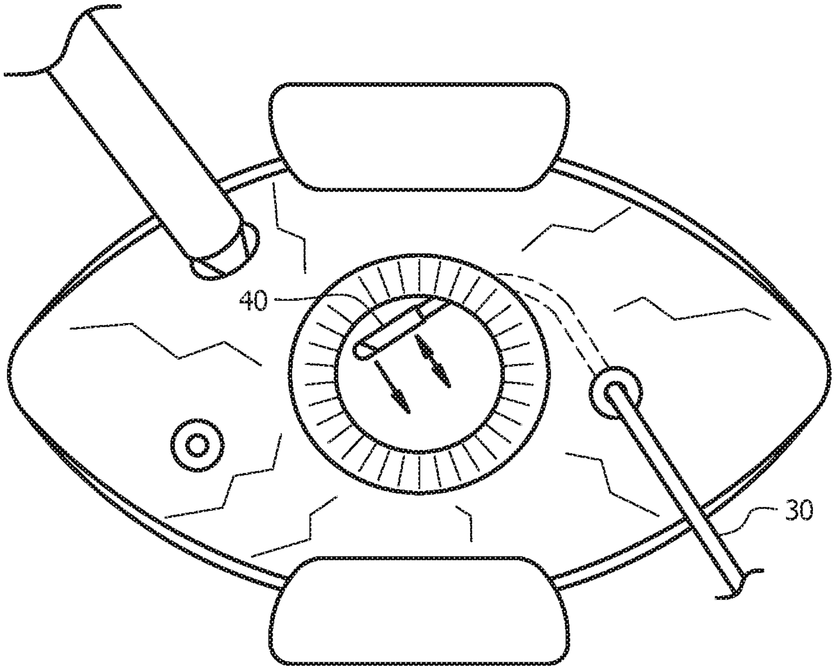
FIG. 9 is an image depicting insertion of the curved shaft embodiment of the device into a patient's eye.
Figure 10:
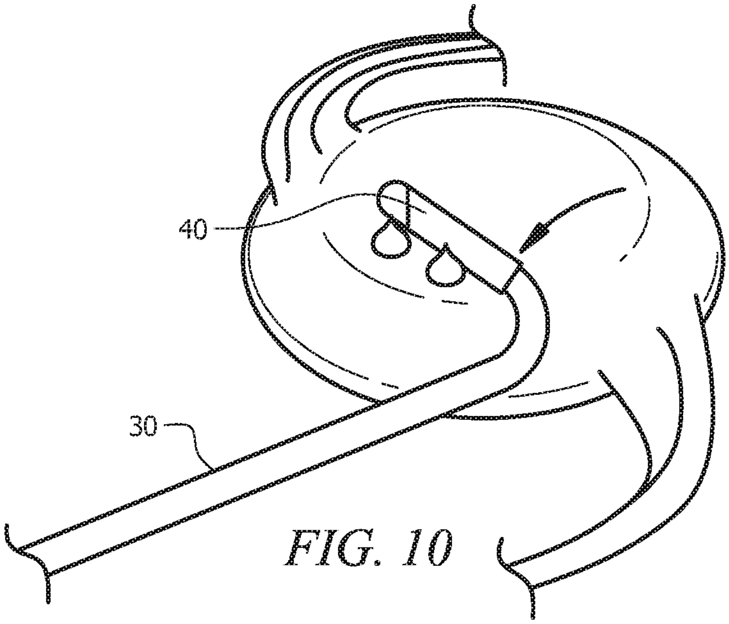
FIG. 10 is an image depicting removal of condensation droplets from the posterior surface of the lens using the curved shaft embodiment of the device.

An alternative embodiment of device 10 is shown in FIGS. 7-10 which does not require a blade deployment mechanism as distal end of shaft 30 is curved at an angle which thus allows blade 40 be oriented at an angle relative to longitudinal axis of shaft 30. In some embodiments, distal end of shaft is curved at about a 90° angle. As shown in FIG. 9, insertion of device 10 into the eye of the patient occurs through an opening in the sclera of the eye. Lid speculum used to keep the eye open is depicted as squares at the top and bottom of the eye. Infusion tube is depicted in the upper left corner with trocar being depicted in the lower right corner of the figure. Opening for device 10 is depicted in right side of sclera of eye. Blade 40 is positioned such that edge 50 is in contact with the posterior surface of the lens. Movement of device 10 is shown as being in a downward motion from the top of the lens to the bottom of the lens at an angle. Alternatively, movement can be in a straight downward motion as depicted in FIG. 10. As shown in FIG. 10, movement of edge 50 of blade 40 effectively removes the condensation/droplets from the posterior surface of the lens thus clearing the viewing field.

Handle and shaft can be solid in this embodiment as there is no need for a blade deployment mechanism.

In conclusion, the device described herein provides a cost-efficient and effective solution to the problem of intraocular lens condensation.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween. Now that the invention has been described,

What is claimed is:

1. A device for removing intraocular lens condensation comprising:

a handle having proximal and distal ends;

a shaft having a proximal and a distal end wherein the proximal end of the shaft is attached to the distal end of the handle; and a flexible rubber-like blade having a smooth surface, a teardrop-shaped cross-section, and a proximal and a distal end; wherein the proximal end of the blade is attached to the distal end of the shaft by a hinge;

wherein the distal end of the blade is tapered relative to the proximal end of the blade; and wherein the blade has at least one longitudinal condensation removal edge.

2. The device of claim 1, further comprising a blade deployment mechanism connected to the blade.

3. The device of claim 2, wherein the blade deployment mechanism is connected to the blade by a wire.

4. The device of claim 2, wherein the blade deployment mechanism is connected to the blade electronically.

5. The device of claim 1, wherein the blade deployment mechanism is selected from the group consisting of a lever, a switch, a button, a wheel, and a slider.

6. The device of claim 1, wherein the shaft is straight.

7. The device of claim 1, wherein the shaft is curved at the distal end.

8. The device of claim 7, wherein the distal end of the shaft is curved about 90° relative to the proximal end of the shaft.

9. A method of removing intraocular lens condensation comprising:

providing a device for removing intraocular lens condensation comprising:

a handle having proximal and distal ends;

a shaft having a proximal and a distal end wherein the proximal end of the shaft is attached to the distal end of the handle; and a rubber-like blade having a proximal and a distal end wherein the proximal end of the blade is attached to the distal end of the shaft;

wherein the blade has at least one longitudinal condensation removal edge;

inserting the device into the eye of a patient;

positioning the device so that the condensation removal edge is in contact with a posterior surface of the lens;

moving the device in a downward motion across the posterior surface of the lens;

wherein movement of the device across the posterior surface of the lens results in removal of the intraocular lens condensation from a surgical viewing field.

10. The method of claim 9, wherein the blade is moveably attached to the shaft by a hinge.

11. The method of claim 10, further comprising a blade deployment mechanism connected to the blade.

12. The method of claim 11, wherein the blade deployment mechanism is connected to the blade by a wire.

13. The method of claim 12, wherein once the device is inserted into the eye of the patient, the blade deployment mechanism is engaged to move the blade to about a 90° angle relative to the shaft.

14. The method of claim 11, wherein the blade deployment mechanism is connected to the blade electronically.

15. The method of claim 9, wherein the shaft is straight.

16. The method of claim 9, wherein the shaft is curved at the distal end.

17. The method of claim 16, wherein the shaft is curved about a 90° angle relative to the proximal end of the shaft.

* * * * *